United States Patent
Shinoda et al.

(10) Patent No.: US 8,999,255 B2
(45) Date of Patent: Apr. 7, 2015

(54) AIR PURIFICATION SYSTEM FOR VEHICLE

(75) Inventors: Yoshihisa Shinoda, Susono (JP); Koichi Hoshi, Susono (JP); Hiroaki Katsumata, Susono (JP); Kazuhiro Sugimoto, Susono (JP); Kayoko Takada, Gotenba (JP); Ippei Fukutomi, Machida (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/501,180

(22) PCT Filed: Dec. 14, 2010

(86) PCT No.: PCT/JP2010/072486
§ 371 (c)(1),
(2), (4) Date: Apr. 10, 2012

(87) PCT Pub. No.: WO2012/081086
PCT Pub. Date: Jun. 21, 2012

(65) Prior Publication Data
US 2013/0256045 A1    Oct. 3, 2013

(51) Int. Cl.
*A61L 9/18* (2006.01)
*B60H 3/06* (2006.01)
(Continued)

(52) U.S. Cl.
CPC . *B60K 13/02* (2013.01); *A61L 9/20* (2013.01); *B01D 53/46* (2013.01); *B01D 53/66* (2013.01); *B01D 2253/102* (2013.01); *B01D 2255/20707* (2013.01); *B01D 2255/802* (2013.01); *B01D 2257/106* (2013.01); *B01D 2257/404* (2013.01); *B01D 2258/06* (2013.01);
(Continued)

(58) Field of Classification Search
USPC .............................................. 422/186.3, 121
See application file for complete search history.

(56) References Cited

U.S. PATENT DOCUMENTS 5,951,957 A * 9/1999 Simpson ........................ 423/219
6,190,627 B1    2/2001 Hoke et al.
(Continued)

FOREIGN PATENT DOCUMENTS

JP    A-03-193117    8/1991
JP    A-09-206558    8/1997
(Continued)

OTHER PUBLICATIONS

International Search Report issued in Application No. PCT/JP2010/072486; Dated Feb. 8, 2011 (With Translation).

*Primary Examiner* — Kishor Mayekar
(74) *Attorney, Agent, or Firm* — Oliff PLC

(57) ABSTRACT

The present invention has an object to put into practical use an air purification system for a vehicle, which incorporates an ozone purifier formed to contain an activated carbon. The air purification system for a vehicle provided by the present invention includes an ozone purifier that is formed to contain an activated carbon therein and disposed on a surface of a vehicle component disposed at a position at which an air flow path is formed while the vehicle is running. The air purification system for a vehicle also includes a purification inhibitor remover that is disposed upstream of the ozone purifier in the above-described flow path, for removing a component inhibiting purification of ozone by the ozone purifier, from the air flowing into the ozone purifier. The ozone purifier may, for example, be disposed on a radiator and the purification inhibitor remover on a condenser or a sub-radiator.

6 Claims, 2 Drawing Sheets

(51) Int. Cl.
*A61L 9/20* (2006.01)
*B01D 53/46* (2006.01)
*B01D 53/66* (2006.01)
*B60K 13/02* (2006.01)
*F02M 27/06* (2006.01)
*F02M 35/02* (2006.01)
*F02M 35/06* (2006.01)
*F02M 35/10* (2006.01)
*F02M 35/16* (2006.01)
*B01J 35/00* (2006.01)

(52) U.S. Cl.
CPC .. *B01D 2259/4566* (2013.01); *B01D 2259/804* (2013.01); *B01J 35/004* (2013.01); *F02M 27/06* (2013.01); *F02M 35/0218* (2013.01); *F02M 35/06* (2013.01); *F02M 35/10013* (2013.01); *F02M 35/161* (2013.01)

(56) References Cited

U.S. PATENT DOCUMENTS

| | | | |
|---|---|---|---|
| 6,200,542 B1 | 3/2001 | Poles et al. | |
| 6,340,066 B1 | 1/2002 | Dettling et al. | |
| 6,569,393 B1 * | 5/2003 | Hoke et al. | 423/219 |
| 6,818,254 B1 | 11/2004 | Hoke et al. | |
| 6,938,684 B2 * | 9/2005 | Iwasaki | 165/135 |
| 7,070,744 B2 * | 7/2006 | Son | 422/186.04 |
| 2001/0019707 A1 | 9/2001 | Okayama et al. | |
| 2001/0055554 A1 | 12/2001 | Hoke et al. | |
| 2002/0071800 A1 | 6/2002 | Hoke et al. | |
| 2003/0059356 A1 | 3/2003 | Hoke et al. | |

FOREIGN PATENT DOCUMENTS

| | | |
|---|---|---|
| JP | A-10-244130 | 9/1998 |
| JP | A-11-500656 | 1/1999 |
| JP | A-2001-347829 | 12/2001 |
| JP | A-2002-514966 | 5/2002 |
| JP | A-2003-515442 | 5/2003 |
| JP | A-2004-321920 | 11/2004 |
| JP | A-2010-029816 | 2/2010 |
| WO | WO 96/22146 A2 | 7/1996 |
| WO | WO 96/22149 A1 | 7/1996 |
| WO | 00/71867 A1 | 11/2000 |
| WO | WO 01/39886 A1 | 6/2001 |

* cited by examiner

AIR PURIFICATION SYSTEM FOR VEHICLE

TECHNICAL FIELD

The present invention relates, in general, to air purification systems for vehicles. The present invention particularly relates to an air purification system for a vehicle, which is capable of directly purifying ozone in the air.

BACKGROUND ART

Ozone that causes photochemical smog is created by photochemical reaction of HC and NOx contained in exhaust gases from automobiles and plants. Thus, reducing emissions of HC and NOx from automobiles is an effective means of holding down creation of ozone and thereby preventing occurrence of photochemical smog. Meanwhile, directly purifying ozone in the air can be another means of preventing occurrence of photochemical smog. Trying not only to reduce emissions of HC and NOx as reactants, but also to purify ozone as a product allows occurrence of photochemical smog to be prevented even more effectively. Against this background, in some areas including California, the U.S., automobiles including air purification systems for vehicles are put into practical use, the system being capable of directly purifying ozone in the air. Such air purification systems for vehicles are specifically called direct ozone reduction (DOR) systems.

The air purification systems for vehicles (DOR systems) that have conventionally been put into practical use incorporate a catalyst that is a metal oxide, such as manganese dioxide, as disclosed in JP-A-2002-514966 and JP-A-2003-515442. Application of a metal oxide catalyst to a radiator into which air flows during vehicle running allows the catalyst to decompose and purify ozone contained in the air.

Not only the manganese dioxide or other metal oxide catalyst, but also an activated carbon is known to have a function of purifying ozone. The ozone reacts with the activated carbon to become carbon dioxide. This reaction takes place even under room temperature, so that the activated carbon can be said to be advantageous in purification conditions, as compared with the metal oxide catalyst that requires a reaction temperature higher than the room temperature.

As of today, however, no air purification systems for vehicles, which use the activated carbon for an ozone purifier, have been put into practical use. Use of the activated carbon for the ozone purifier poses a problem in that purifying performance of the ozone purifier is easy to be degraded. The cause of this problem lies in the function of the activated carbon to adsorb moisture and PM, and NOx and SOx, contained in the air. These substances adsorbed on the activated carbon act as purification inhibitors inhibiting a reaction between the ozone and the activated carbon, seriously degrading the ozone purifying performance of the activated carbon. It is technically possible to recover the purifying performance of the activated carbon. That, however, involves complication of structures of the air purification systems for vehicles and requires a large amount of energy. In using the activated carbon in the air purification systems for vehicles, therefore, how to reduce effects of the purification inhibitors, such as moisture, NOx, SOx, and PM, on the activated carbon is a problem to be solved.

PRIOR ART LITERATURE

Patent Documents

Patent Document 1: JP-A-2002-514966
Patent Document 2: JP-A-2003-515442

SUMMARY OF THE INVENTION

The present invention has been made in view of the foregoing problem and it is an object of the present invention to put into practical use an air purification system for a vehicle, which incorporates an ozone purifier formed to contain an activated carbon. The present invention thus provides an air purification system for a vehicle, which includes, in addition to an ozone purifier formed to contain an activated carbon, a purification inhibitor remover for removing components inhibiting purification of ozone by the ozone purifier (hereinafter referred to as a purification inhibitor). The ozone purifier is disposed on a surface of a vehicle component disposed at a position at which an air flow path is formed while the vehicle is running. The purification inhibitor remover is disposed upstream of the ozone purifier in the above-described flow path. In the arrangement of such an air purification system for a vehicle, the purification inhibitor is removed from an air flowing into the ozone purifier, so that ozone purifying performance of the ozone purifier can be maintained at a high level.

The purification inhibitor remover incorporated in the present invention is not necessarily required to remove the purification inhibitor constantly or make the purification inhibitor harmless through decomposition or synthesis. Ease with which the purification inhibitor is adsorbed onto the ozone purifier varies depending on environmental conditions including temperature and a flow rate. A type of purification inhibitor remover that temporarily captures the purification inhibitor may therefore be used, as long as the purification inhibitor can be prevented from flowing into the ozone purifier under at least a condition in which the purification inhibitor is easily adsorbed onto the ozone purifier. Thus, for example, a NOx adsorbent such as alumina, a NOx adsorption and reduction type catalyst having a NOx reduction function in addition to a NOx adsorption function, or the activated carbon or zeolite may be used for the purification inhibitor remover.

The purification inhibitor remover is disposed in either of the following two preferred modes. In a first mode, when another vehicle component (a second vehicle component) is disposed upstream of the vehicle component on which the ozone purifier is disposed in the flow path, the purification inhibitor remover is disposed on a surface of the second vehicle component. In this case, the vehicle component on which the ozone purifier is disposed is desirable to be a radiator. Further, the second vehicle component on which the purification inhibitor remover is disposed is desirable to be a condenser, a sub-radiator, or a bumper grille. In a second mode, in contrast, the ozone purifier is disposed on, of areas constituting the surface of the vehicle component, an area located downstream in an air flow direction and the purification inhibitor remover is disposed on an area located upstream in the air flow direction. In this case, the vehicle component is desirable to be a radiator.

A desirable relationship exists relating to installation conditions between the ozone purifier and the purification inhibitor remover. For one, a total contact area of the purification inhibitor remover relative to the air is greater than that of the ozone purifier relative to the air. In addition, if the ozone purifier and the purification inhibitor remover are each disposed on respective vehicle components, in particular, heat exchangers having large numbers of fins, the heat exchanger on which the purification inhibitor remover is disposed may have a fin pitch narrower than a fin pitch of the heat exchanger on which the ozone purifier is disposed. Adsorption of the purification inhibitor onto the activated carbon occurs by diffusion reaction. If the purification inhibitor remover is disposed based on the above-described relationship, part of the purification inhibitor that has not been purified by the purification inhibitor remover flows directly past the ozone purifier without contacting the ozone purifier. Even if the purification inhibitor remover fails to remove all purification inhibitors, further deterioration of the ozone purifier can be avoided.

For the purification inhibitor remover, a photocatalyst may be used, in addition to those exemplified earlier. The photocatalyst absorbs ultraviolet light to thereby exhibit superhydrophilicity, becoming to adsorb moisture in the air onto a surface thereof. In addition, hydrophilic NOx, SOx, or PM is adsorbed onto the surface. The NOx, SOx, or PM adsorbed flows down with the moisture, being removed from the surface of the purification inhibitor remover. Specifically, with the purification inhibitor remover including a photocatalyst, not only the purification inhibitor can be adsorbed, but also the purification inhibitor adsorbed can be discharged outside the system through a self-cleaning action by the photocatalyst. In this case, it is desirable that the vehicle include an ultraviolet irradiation device, so that the photocatalyst can be irradiated with ultraviolet rays by the ultraviolet irradiation device under a condition in which there is a short supply of light intensity, such as in the nighttime.

MODES FOR CARRYING OUT THE INVENTION

First Embodiment

A first embodiment of the present invention will be described below with reference to the accompanying drawings.

Figure 1:
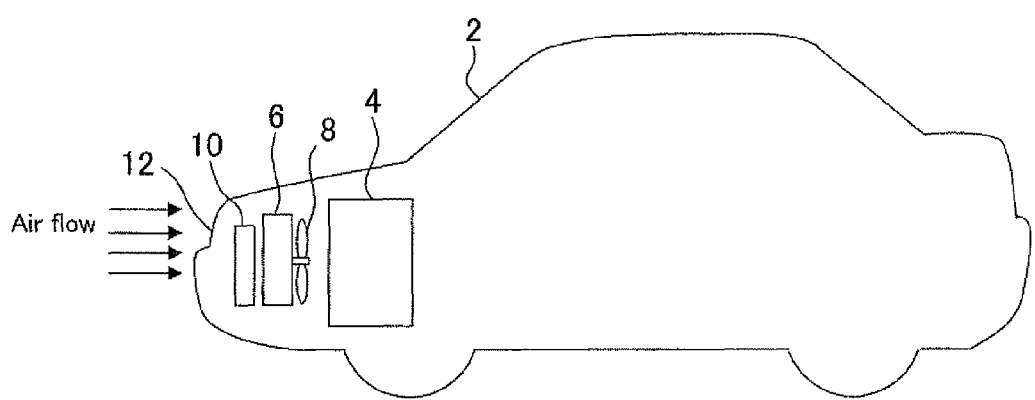
FIG. 1 is a schematic view showing an arrangement of an automobile to which an air purification system for a vehicle according to each of embodiments of the present invention is applied.

FIG. 1 is a schematic view showing an arrangement of an automobile to which an air purification system for a vehicle according to the embodiment of the present invention is applied. The air purification system for a vehicle is applied to an automobile 2 including an internal combustion engine 4 as a power unit. Exhaust gases discharged from the internal combustion engine 4 include HC and NOx. Ozone is created through photochemical reaction with HC and NOx as reactants. The air purification system for a vehicle is applied to the automobile 2 including the internal combustion engine 4 to thereby purify ozone in the air while the automobile 2 is running. Thereby, environmental impact from the automobile 2 can be reduced.

The automobile 2 includes a radiator 6 disposed forwardly of the internal combustion engine 4, and a condenser 10 of an air conditioner disposed forwardly of the radiator 6. The radiator 6 has a radiator fan 8 attached thereto on a back side thereof. While the automobile 2 is running, the air is drawn in through a bumper grille 12 on a front surface of the automobile 2. The air drawn in flows through the condenser 10 and the radiator 6 before being discharged rearwardly. In addition, rotation of the radiator fan 8 forms a flow path of the air that flows from the bumper grille 12 through the condenser 10 to the radiator 6 even while the automobile 2 remains stationary.

Figure 2:
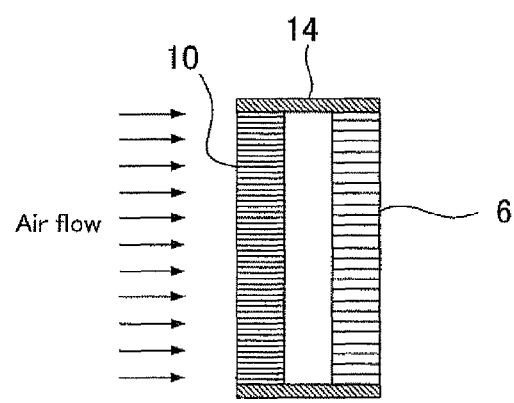
FIG. 2 is a schematic view showing a portion particularly related to an air purification system for a vehicle according to a first embodiment of the present invention, as extracted from the automobile shown in FIG. 1.

FIG. 2 is a schematic view showing a portion particularly related to the air purification system for a vehicle according to the embodiment, as extracted from the automobile 2. A core of the radiator 6 has louvered fins and a core of the condenser 10 also has louvered fins. The condenser 10 has a fin pitch set to be narrower than a fin pitch in the radiator 6. A gap between the radiator 6 and the condenser 10 has a side surface covered with an SUS plate 14. This prevents the air from flowing into the gap by way of the side surface, so that only the air that has flowed through the condenser 10 may flow to the radiator 6.

In the arrangement of the air purification system for a vehicle shown in FIG. 2, the louvered fins of the radiator 6 is coated with an ozone purifier formed to contain an activated carbon, and the louvered fins of the condenser 10 is coated with a purification inhibitor remover. The ozone purifier may be formed of only the activated carbon or formed to contain a catalyst of some sort in addition to the activated carbon. The purification inhibitor remover refers to a substance that can remove, from the air even temporarily, components that inhibit the ozone purifier from purifying ozone, specifically, moisture, NOx, SOx, and PM. By disposing such a purification inhibitor remover upstream of the radiator 6 in the air flow path, specifically, upstream of the ozone purifier, a purification inhibitor can be removed from the air flowing in the ozone purifier, so that the activated carbon contained in the ozone purifier can be prevented from being deteriorated.

Suitable examples of the purification inhibitor remover include NOx adsorbents such as alumina, NOx adsorption and reduction type catalysts, zeolite, and activated carbons similar to the ozone purifier. An example of the NOx adsorption and reduction type catalyst comprises a carrier formed of $ZrO_2$, $CeO_2$, and Y-type zeolite loaded with Rh. As is known from these exemplifications, the purification inhibitor remover incorporated in the air purification system for a vehicle is not necessarily required to remove the purification inhibitor constantly or make the purification inhibitor harmless through decomposition or synthesis. A type of purification inhibitor remover that temporarily captures the purification inhibitors may be used, as long as the purification inhibitors can be prevented from flowing into the ozone purifier under at least a condition in which the purification inhibitors are easily adsorbed onto the ozone purifier. The purification inhibitor remover is desirable to be a combination of exemplified materials appropriately combined so as to remove all components of moisture, NOx, SOx, and PM.

If the purification inhibitor remover contains a NOx adsorbent, NOx, SOx, and moisture in the air that passes through the condenser 10 can be captured through adsorption. The purification inhibitors adsorbed by the NOx adsorbent are released as a temperature of the condenser 10 rises and a flow rate of air passing through the condenser 10 increases. The purification inhibitors released will eventually flow in the radiator 6 disposed downstream; however, it is less likely that the purification inhibitors that flow in will be adsorbed onto the ozone purifier. This is because of the following reason: specifically, since there is no difference in adsorption and release characteristics of the purification inhibitors between the NOx adsorbent and the activated carbon in the ozone purifier, a condition in which the purification inhibitors are easily released from the NOx adsorbent is, to state it another way, also a condition in which the purification inhibitors are hard to adsorb onto the ozone purifier.

If the purification inhibitor remover contains the activated carbon or zeolite, moisture and PM in the air can be captured within pores. The moisture captured by the activated carbon or zeolite is released as the temperature of the condenser 10 rises and the flow rate of air passing through the condenser 10 increases; however, because of the reason mentioned earlier, it is less likely that the moisture that is released will be adsorbed onto the downstream ozone purifier. PM, meanwhile, is constantly accumulated in the pores of the activated carbon or zeolite without being released, so that a situation will eventually arise in which PM can no longer be accumulated. It is nonetheless possible to avoid any substantive problem by coating the radiator 6 with a sufficient amount of activated carbon or zeolite to thereby achieve a good capacity to accumulate PM.

According to the relationship of the fin pitch between the radiator 6 and the condenser 10 employed in the embodiment, a situation can be avoided in which, even if the purification inhibitor remover fails to remove all of the purification inhibitors, the ozone purifier is thereby deteriorated further. This is because of the following reason: specifically, a reaction involved in the purification inhibitors being adsorbed onto the activated carbon of the ozone purifier is a diffusion reaction and it is less likely that the purification inhibitors not adsorbed onto in the condenser 10 having a narrow fin pitch (specifically, a diffusion distance is short) will be adsorbed onto in the radiator 6 having a wide fin pitch (specifically, the diffusion distance is long). In the air purification system for a vehicle, the purification inhibitors not purified by the purification inhibitor remover applied to the condenser 10 flow directly through the radiator 6 without contacting the ozone purifier applied to the radiator 6.

Second Embodiment

A second embodiment of the present invention will be described below with reference to the accompanying drawings.

Figure 3:
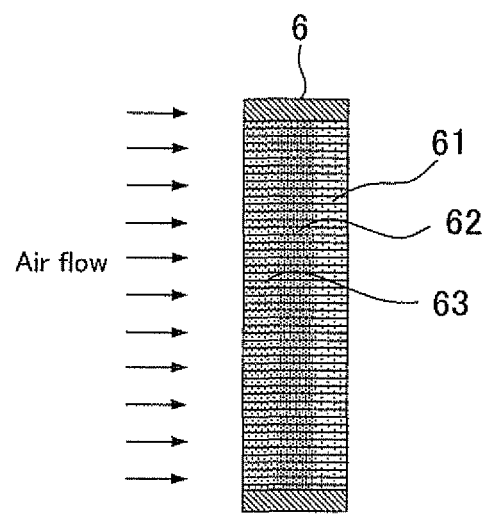
FIG. 3 is a schematic view showing a portion particularly related to an air purification system for a vehicle according to a second embodiment of the present invention, as extracted from the automobile shown in FIG. 1.

FIG. 3 is a schematic view showing a portion particularly related to an air purification system for a vehicle according to this embodiment, as extracted from the automobile 2 shown in FIG. 1. A radiator 6 of this embodiment includes a core that is divided into three areas 61, 62, 63 in the air flow direction. The area 61 located most downstream of these is the closest to the internal combustion engine and has a relatively high temperature because of its being heated by radiation from the internal combustion engine. In the air purification system for a vehicle, the most downstream area 61 is coated with an ozone purifier formed to contain an activated carbon, so that the temperature of the ozone purifier can be quickly raised to a level higher than room temperature immediately after the internal combustion engine is started. The activated carbon contained in the ozone purifier exhibits purification performance even under room temperature unlike the metal oxide catalyst. The purification performance improves further as the temperature increases to a level higher than the room temperature. In the air purification system for a vehicle, therefore, a high ozone purification performance can be obtained immediately after the start.

In the air purification system for a vehicle, the area 62 located in the middle of the radiator 6 is coated with a NOx adsorbent and the area 63 located most upstream is coated with a PM adsorbent such as the activated carbon and zeolite. Specifically, an arrangement is made in which PM that is hard to diffuse is removed in a first stage and NOx and SOx are removed in a second stage. Moisture can be removed by both the NOx adsorbent and the PM adsorbent. In addition, in the arrangement shown in FIG. 3, each of louvered fins in the area 62 and louvered fins in the area 63 is adapted to have a total surface area larger than a total surface area of louvered fins in the area 61. This is done to make a total contact area of the NOx adsorbent or the PM adsorbent relative to the air larger than a total contact area of the ozone purifier relative to the air.

In the air purification system for a vehicle, the purification inhibitor remover is disposed upstream of the ozone purifier in the air flow path as in the first embodiment. This allows the purification inhibitor to be removed from the air flowing in the ozone purifier, helping inhibit the activated carbon contained in the ozone purifier from being deteriorated. In addition, the total contact area of the NOx adsorbent or the PM adsorbent relative to the air is larger than the total contact area of the ozone purifier relative to the air. As a result, the purification inhibitor not purified by the NOx adsorbent or the PM adsorbent flows directly through the downstream ozone purifier without contacting the ozone purifier. Consequently, should the NOx adsorbent or the PM adsorbent fail to purify all of the purification inhibitors, the ozone purifier can be avoided from being thereby further deteriorated.

Third Embodiment

Lastly, a third embodiment of the present invention will be described below with reference to the accompanying drawings.

Figure 4:
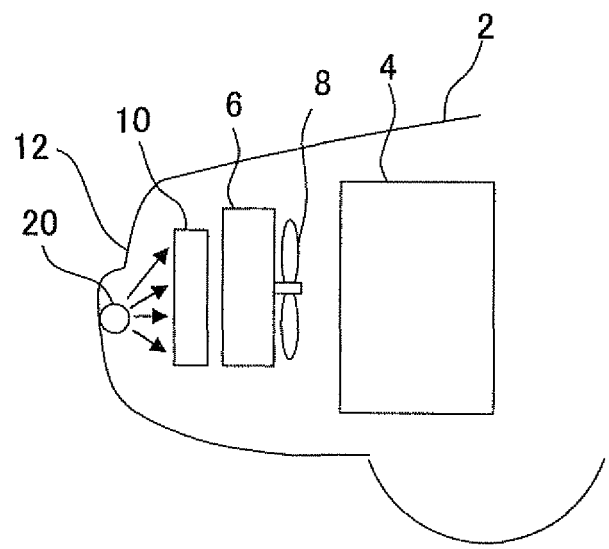
FIG. 4 is a schematic view showing a portion particularly related to an air purification system for a vehicle according to a third embodiment of the present invention, as extracted from the automobile shown in FIG. 1.

FIG. 4 is a schematic view showing a portion particularly related to an air purification system for a vehicle according to this embodiment, as extracted from the automobile 2 shown in FIG. 1. In this air purification system for a vehicle arranged as shown in FIG. 4, a radiator 6 has louvered fins that are coated with an ozone purifier formed to contain an activated carbon and a condenser 10 has louvered fins that are coated with a photocatalyst formed of titanium oxide. Specifically, the air purification system for a vehicle incorporates the photocatalyst as the purification inhibitor remover. Furthermore, an ultraviolet lamp 20 that emits ultraviolet rays toward the condenser 10 is disposed on an inside of a bumper grille 12. The ultraviolet lamp 20 is operative under a condition in which there is a short supply of light intensity, such as in the nighttime, emitting the ultraviolet rays toward the condenser 10.

In the air purification system for a vehicle, the photocatalyst that absorbs ultraviolet light to thereby exhibit superhydrophilicity adsorbs moisture in the air. In addition, the photocatalyst can adsorb hydrophilic NOx, SOx, or PM onto a surface of the moisture. The NOx, SOx, or PM adsorbed onto the moisture on a surface of the photocatalyst flows down the condenser 10 with the moisture, being discharged outside the system. In the air purification system for a vehicle, such a self-cleaning action by the photocatalyst allows performance for removing the purification inhibitor to be maintained constantly, so that ozone purification performance of the ozone purifier can be maintained at a high level.

Miscellaneous

The present invention is not limited to the above-described embodiments. The present invention extends to various modifications that fall within the scope and spirit of the present invention. For example, in the first and third embodiments, the purification inhibitor remover is applied to the condenser; however, on a vehicle including a sub-radiator, the purification inhibitor remover may be applied to the sub-radiator. Alternatively, the purification inhibitor remover may be applied to the bumper grille.

In the first embodiment, the condenser and the radiator have different fin pitches. The condenser may still have a cell density greater than a cell density of the radiator. Alternatively, a volume of a portion to which the purification inhibitor remover is applied in the condenser may be larger than a volume of a portion to which the ozone purifier is applied in the radiator.

DESCRIPTION OF REFERENCE NUMERALS

2 Automobile
4 Internal combustion engine
6 Radiator
8 Radiator fan
10 Condenser
12 Bumper grille
14 SUS plate
61 Ozone purifier coating area
62 NOx adsorbent coating area
63 PM adsorbent coating area

The invention claimed is:

1. An air purification system for a vehicle, comprising:
a vehicle component that is disposed at a position at which an air flow path is formed while the vehicle is running;
an ozone purifier that is disposed on a surface of the vehicle component, the ozone purifier being formed to contain an activated carbon therein; and
a purification inhibitor remover that is disposed separately from the ozone purifier upstream of the ozone purifier in the flow path, for removing a component inhibiting purification of ozone by the ozone purifier, from the air flowing into the ozone purifier, wherein:
the purification inhibitor remover is disposed on a surface of a second vehicle component disposed upstream of the vehicle component in the flow path,
the second vehicle component comprises a heat exchanger having a large number of fins in a portion through which the air flows,
the second vehicle component has a fin pitch narrower than a fin pitch of the vehicle component,
the vehicle component consists of a radiator, and
the vehicle component has only the ozone purifier disposed on the surface.

2. The air purification system for a vehicle according to claim 1,
wherein: the second vehicle component comprises any of a condenser, a sub-radiator, and a bumper grille.

3. The air purification system for a vehicle according to claim 1,
wherein: the ozone purifier is disposed on, of areas constituting the surface of the vehicle component, an area located downstream in an air flow direction; and
the purification inhibitor remover is disposed on an area located upstream in the air flow direction.

4. The air purification system for a vehicle according to claim 1,
wherein: a total contact area of the purification inhibitor remover relative to the air is greater than a total contact area of the ozone purifier relative to the air.

5. The air purification system for a vehicle according to claim 1,
wherein: the purification inhibitor remover includes a photocatalyst.

6. The air purification system for a vehicle according to claim 5, further comprising:
an ultraviolet irradiation device for irradiating the purification inhibitor remover with ultraviolet rays.

* * * * *